Figure 1:
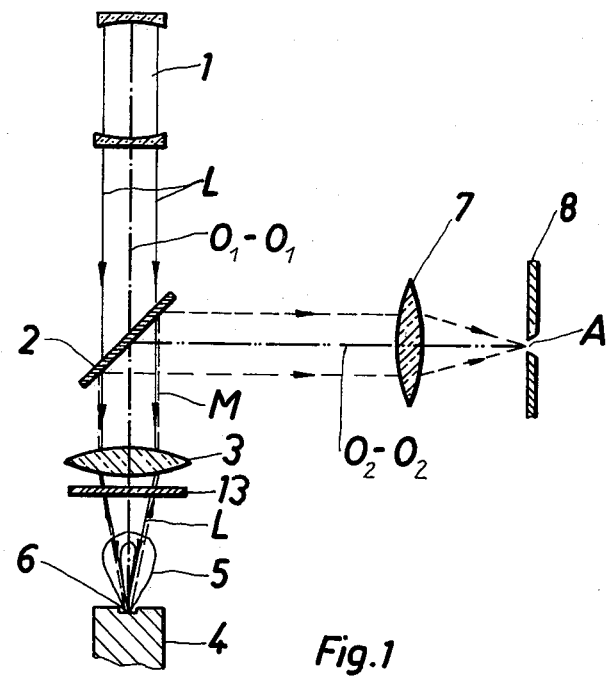

United States Patent [19]

Quillfeldt

[11] 4,182,574

[45] Jan. 8, 1980

[54] ARRANGEMENT FOR CARRYING OUT LASER SPECTRAL ANALYSIS

[75] Inventor: Winfried Quillfeldt, Jena-Lobeda, German Democratic Rep.

[73] Assignee: Jenoptik Jena G.m.b.H., Jena, German Democratic Rep.

[21] Appl. No.: 796,904

[22] Filed: May 13, 1977

[30] Foreign Application Priority Data

May 27, 1976 [DD] German Democratic Rep. ............................... 1193041
Oct. 19, 1976 [DD] German Democratic Rep. ............................... 1195334
Nov. 26, 1976 [DD] German Democratic Rep. ............................... 1195979

[51] Int. Cl.² .......................... G01J 3/30; G01J 3/42
[52] U.S. Cl. ................................................. 356/318
[58] Field of Search .................. 356/36, 73, 85-87

[56] References Cited

FOREIGN PATENT DOCUMENTS 2219191 of 1973 Fed. Rep. of Germany ............ 356/86
160859 of 1964 U.S.S.R. .................................. 356/86

OTHER PUBLICATIONS

Karyakin et al., "The Use of a Pulsed Laser in Atomic Absorption Spectrographic Analysis", Jr. of Analytical Chem. of the USSR, Translation of Zhurnal Analiticheskoi Khimii, vol. 23, 1968, pp. 807-808.
Karyakin et al., "The Use of the Laser in the Atomic Absorption Analysis", Conf. 17th Intern. Spectroscopy Coll., vol. 1, Florence, Italy, 9-73, pp. 403-406.
Strobel, H. A., Chemical Instrumentation: A Systematic Approach, 2nd Ed., Addison—Wesley, 1973, pp. 442-424.
Analytical Chem. vol. 50, No. 5, 4-1978, pp. 309R, abstract of Matousek & Orr article.

*Primary Examiner*—John K. Corbin
*Assistant Examiner*—Wm. H. Punter

[57] ABSTRACT

The invention concerns an arrangement for enabling laser spectral analysis of chemical components contained in a target material, by utilizing the respective line spectra of the atoms involved.

A laser beam is focused by an optical system upon the surface of the target material to evaporate portions thereof and to form a material cloud which is excited in the vicinity of the laser focus to emit a radiation.

The focus itself emits a continuous radiation which passes said cloud along the longest extension of the latter and is imaged by the optical system into a spectrograph, where an absorption spectrum of the target material is produced. Simultaneously, an emission spectrum of the target material is imaged into the spectrograph when the light emitted from the material cloud at right angles to the direction of the focused laser beam is utilized.

In this manner the evaluation of spectra is considerably simplified. The inventional arrangement is useful in a wide field of applications in industry and research, such as metallography, chemistry, biology and others.

4 Claims, 6 Drawing Figures

ARRANGEMENT FOR CARRYING OUT LASER SPECTRAL ANALYSIS

The invention concerns an arrangement which enables spectral analysis under use of a laser, the radiation from which, focused upon a target material, evaporises portions thereof, which then emit an atomic radiation subject to spectral analysis.

Previous spectral analysis arrangements which include a laser, employ the latter to evaporise a radiated target material to be analysed and a spectroscope provided with the accessories necessary to investigate the radiations typical of the composition of the target material. Very often these arrangements are provided with additional means, such as an electric spark discharge, to excite the evaporised target material.

In the event of the emission spectral analysis the radiation emitted from the evaporised and excited sample material is imaged into the aperture plane or into a lens system of a spectroscope for investigation of the emission spectrum. In contrast thereto the absorption spectroscopy utilizes the laser focal spot and the crater, respectively, upon or in the target surface as a light source, the continuous radiation therefrom penetrates the material cloud, that is, the evaporised target material to be analysed, where the wavelengths typical of the material composition are absorbed.

So in a simple manner the material composition of a target can be determined from the absorption spectrum and its resonance lines.

The crater is a very practicable light source because there, and in the vicinity thereof, the highest temperature in the material cloud exists and, hence, a very intense and continuous radiation is emitted.

Further known arrangements use a separate light source for emitting a primary radiation.

The arrangements which do without an additional light source have the disadvantage that the radiation which passes the material cloud includes an angle relative to the longitudinal axis. This means a reduction of the length of the light path which the continuous radiation travels through the material cloud so that the radiation absorption is also reduced.

Furthermore, such arrangements render it difficult to observe the target material and, hence, an adjustment to optimal values as to emission and absorption, respectively, is also complicated.

The use of an additional light source partially eliminates these drawbacks, however, the expenditures as to the apparatus required and the liability towards interferences do likewise increase.

It is an object of the present invention to obviate the above disadvantages.

It is a further object of the present invention to provide an arrangement which permits a high efficiency of a spectro-analyse at comparatively low expenditures concerning apparatus requirements.

It is still a further object of the invention to provide an arrangement in which the radiation to be analysed passes a material cloud at a considerably long path and thus is subject to a desired severe absorption at those wavelengths, which are typical of the respective material composition resonance lines.

These and other objects are realised by an arrangement for enabling laser spectro-analysis which substantially comprise a laser light source for emitting coherent light, which supplies the energy to evaporise and to excite a target material to emit a radiation, an optical means for focusing the coherent light on to a target material to be analysed, and a spectroscope for investigation of the absorption spectrum.

According to the invention an optical means including the focusing means is provided in the optical path between the laser and the target material to be analysed in order to image the focal spot,—produced by the light beam on the target material surface, so to excite the emission of a radiation,—into the aperture of a spectrograph. On its way, the emitted radiation passes the target material cloud.

Advantageously, an additional imaging system is provided having an optical axis at right angles to the optical focusing system axis.

Said additional imaging system images the light emitted from the evaporised and excited target material at right angles to the direction of the laser light beam also into the aperture of the spectrograph.

Thus it becomes feasible to detect the atomic emission spectrum simultaneously with the atomic absorption spectrum. Furthermore, it is an advantage to employ a lens as an optical focusing system.

It is still a further advantage to apply a mirror objective as an optical focusing means.

Such objectives have the advantage compared to lens objectives that these offer an improved color compensation. It is a particular advantage when means are provided for directing the propagation direction and the vapor density of the material cloud in the range of the material vapor cloud.

It is a final advantage when samples to be analysed are supported by a material the continuous spectrum of which is known.

Figure 2:
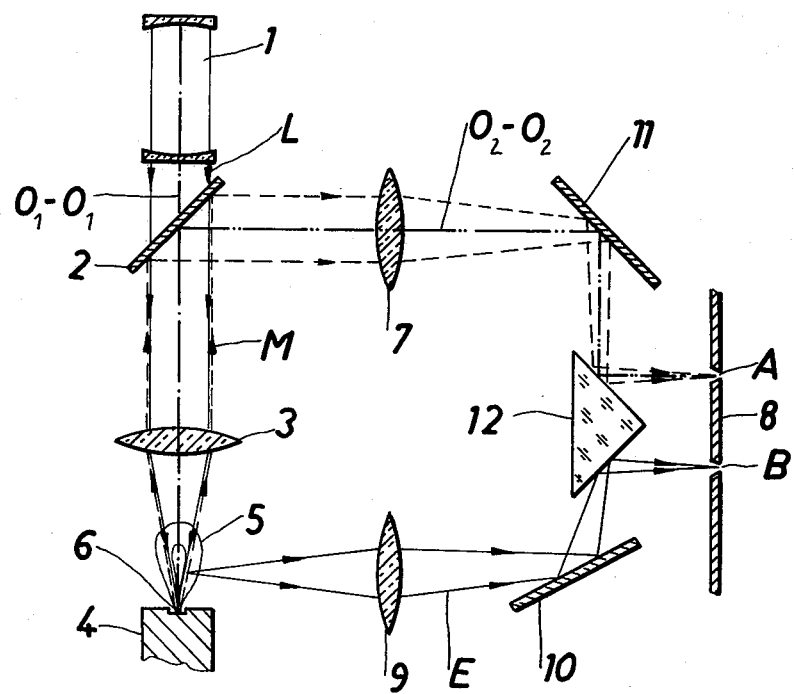
Figure 3:
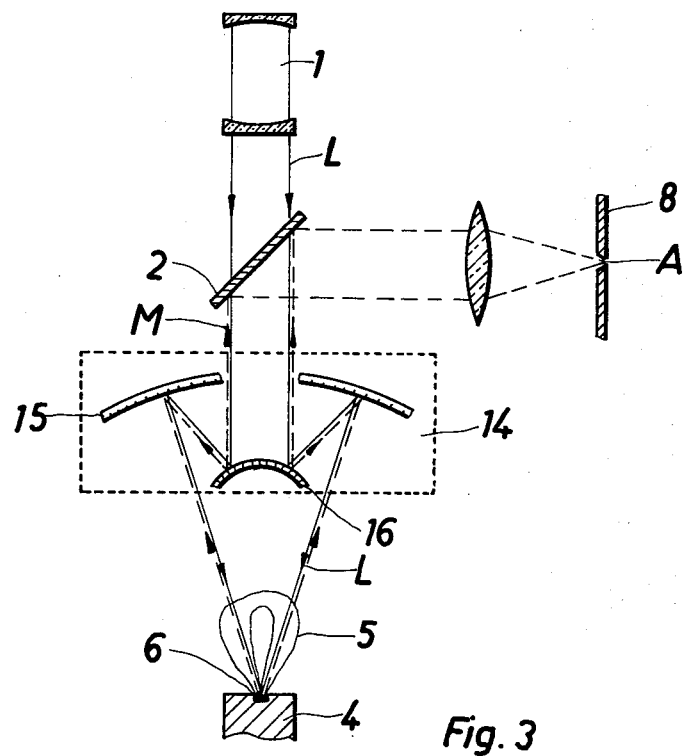
Figure 4:
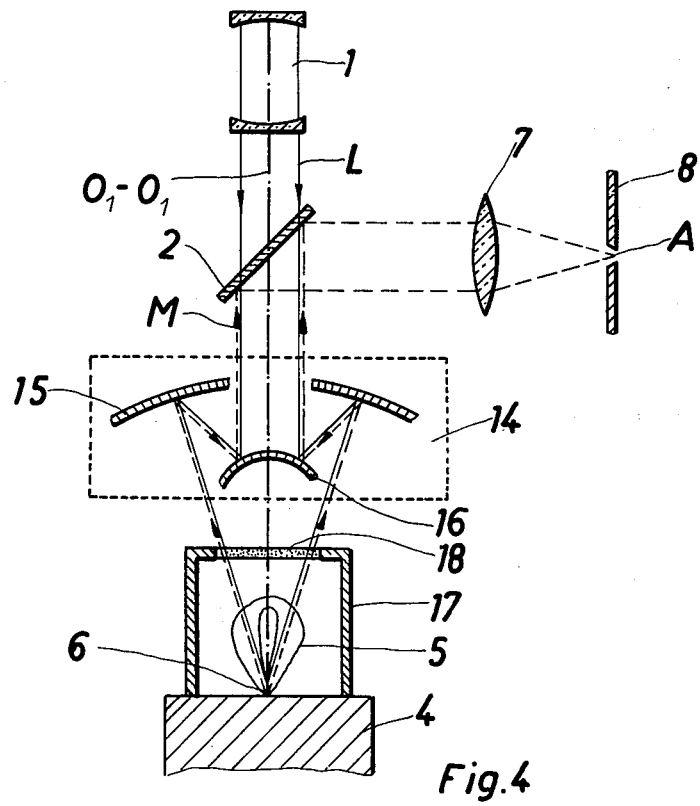
Figure 5:
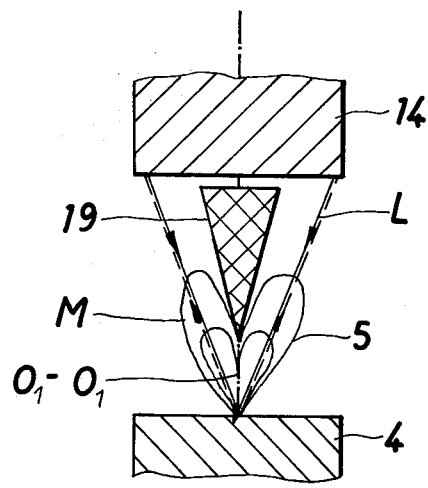
Figure 6:
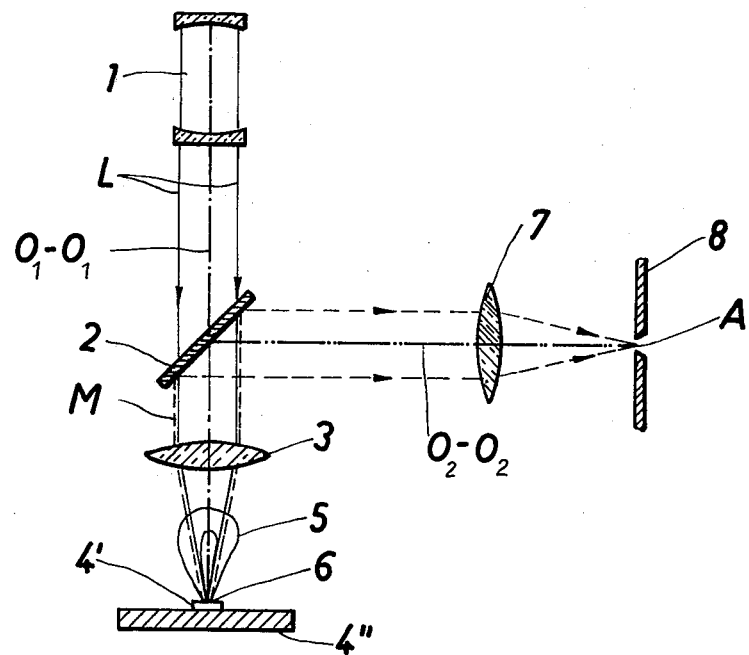

In order that the invention may be more readily understood reference is made to the accompanying drawings which illustrate diagrammatically and by way of example six embodiments thereof and in which:

FIG. 1 is a schematical view of an inventional arrangement for laser spectral analysis of target materials according to the absorption method, FIG. 2 a schematical view of an arrangement for laser microspectral analysis of a target material including means to simultaneously record the emission and absorption spectrum, FIG. 3 a schematical view of an arrangement for determination of the atomic absorption spectrum of a target material in analogy in FIG. 1, including a mirror system for focusing the laser beam upon the surface of a target material, FIG. 4 a schematical view of the arrangement of FIG. 3, including a cell of variable internal pressure for receiving the target material, FIG. 5 a schematical view of a target material cloud separated by a cone located between a mirror system and a target material to be analysed according to FIG. 3, and FIG. 6 a schematical view of an arrangement according to FIG. 1 for analysis of a micro-sample by use of the laser atom absorption spectral analysis.

In FIG. 1 a laser 1, preferably emitting light from the spectral range of red produces a laser beam L which is directed through a reflector 2 tilted relative to an optical axis $0_1$—$0_1$ and focused by a lens objective 3 upon a target material 4 to be analysed.

The reflector 2 is transparent with respect to the laser radiation.

A portion of the target material 4 is, due to the considerable energy involved, evaporised when the laser beam impinges on the material 4 generating a material cloud 5 which burst-like expands.

A heated crater 6 forms at the place of impingement which emits a radiation M, indicated by a dashed line. The radiation M which is of a continuous spectrum passes the plasma cloud 5. The radiation portion outside the laser radiation wavelength is reflected at the reflector 2 along an optical path $0_2$—$0_2$ to a condenser lens 7 which directs the radiation M into the aperture 8 of a not shown spectrograph.

When passing the plasma cloud 5 a portion from the continuous spectrum radiation M is absorbed so that the spectrum including the absorption lines typical of the respective material composition appear in the image plane. The determination of the concentration of the individual components is obtained by measurement of the attenuation which the light of an absorbing line is subject to when passing the material cloud.

Since the target material cloud is radiated parallel to its longitudinal extension the absorption the radiation M is subject to is increased in the range of the resonance lines, and thus the detection sensitivity of the absorption method is improved.

The aperture of the lens 3 is so dimensioned that the laser radiation is of high density on the target side, and that a considerable portion of the generated continuous spectrum radiation is involved for being directed via the partially transmissive reflector 2 to the spectrograph. A transparent plano-parallel protective plate 13 is arranged in the optical path between the target material 4 and the lens 3.

A protective device can also be an objective attachment provided with a suitably dimensioned opening opposite to the objective rear face, considered in the direction of light propagation.

FIG. 2 is a slightly varied arrangement of FIG. 1. In addition to FIG. 1 the arrangement is provided with an optical system 5 for collecting the radiation (beam E) emitted from the evaporised and excited target material and for directing said radiation via a deviating reflector 10 and a deviating prism 12 into the opening B of the spectrograph aperture 8.

The continuous spectrum radiation M is directed via a deviating reflector 11 and a deviating prism 12 into the slit opening A of the spectrograph aperture 8. Two parallel spectral images are produced in this manner in the imaging plane of the spectrograph, one of said spectra represents an absorption spectrum, the other one the emission spectrum of the target material.

The simultaneous registration of both spectra has the advantage of a quick detection of important typical spectral lines and, hence, a rapid qualitative determination of the components contained in the target material.

Furthermore such an arrangement permits a rapid and precise quantitative determination of chemical components concerned by means of an intensity measurement of the spectral lines of the emission spectrum and absorption spectrum.

In a number of applications it is advantageous to include the IR and UV spectral range into the investigation of the chemical components of a material.

To this purpose lenses of a respective spectral transmissivity such as quartz lenses are employed.

It is, however, disadvantageous that lens objectives are not compensated for achromasy in the wavelength concerned, that is, different foci will occur between the radiation emitted from the laser beam and the continuum radiation from the ultraviolet to the bule wavelengths range.

Such different foci can, however, be utilized to employ simultaneously the lens objective as a condenser.

To achieve this, the lens objective is arranged relative to the target material and to the spectrograph aperture in such a manner that the target side focal length, for example, for a ruby laser of $\lambda_1 = 694$ nm, coincides with the target side interception, with respect to a mean wavelength of the continuum radiation, for example, $\lambda_2 \sim 300$ nm.

The distance between the objective 3 and the aperture 8 of the spectrograph is identical to the spectrograph side intercept of the lens objective with respect to a mean wavelength $\lambda_2$.

This event ensures that the laser beam is focused upon the target material surface and said surface, in turn, is sharply imaged into the plane of the spectrograph aperture, with respect to a mean wavelength of the continuum radiation.

FIG. 3 is another arrangement for producing an absorption spectrum of a material cloud generated by a laser beam.

The lens objective of FIG. 1 is replaced by a mirror system 14 for focusing the laser beam L and for imaging the heated craters 6 into the aperture 8.

The mirror system 14 is constituted of a centrally pierced concave reflector 15 and a convex reflector 16.

The focal length is the same with respect to all wavelengths concerned, when a mirror system is employed.

Such a mirror system ensures that only the continuous wavelength radiation which is generated directly upon the target surface is imaged upon the aperture 8, and interferences due to external radiations are eliminated.

This arrangement, however, involves that a considerable portion of the material cloud, when expanding, intrudes into the central obscuration portion of the mirror system and, hence, the radiation from this portion does not arrive at the image path.

Accordingly, this portion cannot be utilized for obtaining spectral informations.

As schematically shown in FIGS. 4 and 5 particular means are provided to control the expansion direction and the material cloud density.

In FIG. 4 a material cloud 5 expands in a chamber 17 provided with a radiation entrance window 18. The interiour chamber pressure may vary between the ambient pressure and about 10 Torr. Depending on the gas pressure the material cloud takes a torch-shape or that of a hemisphere.

In this manner the portion of the material cloud 5 intruding into the central illuminator portion of the mirror system can be considerably reduced, and, in consequence thereof, most of the radiation, passing the material cloud can be exploited for obtaining spectral informations.

Since the amount of the radiation absorption and radiation emission also depends on the density of the evaporised, atomised and ionised sample material, a suitable selection of the interiour pressure enables the adjustment of optimum conditions to carry out absorption analysis or to excite the material cloud to radiation emission.

In FIG. 5, a cone 19 is arranged between the mirror lens 14 and the target material 4 about an optical axis $0_1$—$0_1$. The cone 19, which covers the range of central obscuration, divides a plasma cloud 5.

In this alternative manner, with respect to FIG. 4, the expansion direction of the plasma cloud 5 is controled. When only minor portions of a target material to be analysed are at one's disposal an analyse is difficult, since the extension of the plasma cloud and, hence, the absorption range is very small.

The relative detection sensitivity of the arrangement is further reduced due to impurities which, originating from the target material holder, displace and attenuate the already small material cloud.

Therefore, in FIG. 6 an arrangement for use in the atom absorption analysis, according to FIG. 1, includes further means which permits the investigation also of micro-target materials.

The laser beam L is focused, in analogy to FIG. 1 after passage through the tilted reflector 2, by a lens 3 upon a micro sample 4' which is mounted on a sample holder 4".

The holder material can be, for example, a tungsten flat material which, on the one hand, provides an intensive radiation of a continuous spectrum and, on the other hand, only a few absorption lines.

The micro sample material 4' and the holder material 4" are evaporised by the focused laser beam, which forms a heated crater 6 at the place of the more or less completely evaporised sample material 4'.

The heated crater 6 emits a radiation of a continuous spectrum which passes the material cloud 5. The absorption spectrum is subsequently recorded in known manner. Hence, only the few known spectral lines from the holder material appear in the spectroscope.

Therefore in such an event it is not necessary to analyse the spectrum of the environmental radiation and of the holder material, respectively, so to find out the chemical composition thereof by a second laser pulse.

Preferably, the sample material is secured to the sample holder by an organic adhesive, the material of which has only a few absorption lines.

The invention is not restricted to the above embodiments which only reveal the principle underlying the invention. So the quality, particularly the line intensity and line definition of the absorption spectrum and emission spectrum may be increased in that the material cloud is additionally excited and the atoms, respectively, enhanced by a spark discharge or any other suitable high frequency electrode-less discharge (frequency of $f = 10 \ldots 100$ MHz).

An additional laser beam focused into the plasma cloud satisfies the same purpose.

Apart from the density of the atomic vapor, the degree of absorption also depends on the density of the excited ionised particles and the spread material particles, as well as on their distribution behaviour as a function of space and time.

When the expansion of the material cloud is accomplished by an electric field of a plate condenser, or even in a magnetic field, then the ions and the electrons can be separated and, due to the reduced material density in the plasma cloud, the absorption can be reduced.

I claim:

1. An arrangement for enabling laser spectral analysis, comprising about an optical axis $0_1$—$0_1$
   a laser light source for emitting a beam of coherent light,
   a first optical means for focusing said beam upon a target material to be analysed,
   the energy conveyed by said beam being sufficient to evaporise said target material and to generate a material cloud expanding from the surface of said target material,
   said laser beam simultaneously producing a focal spot in said target material surface, and heating said spot to incandescence to emit a radiation,
   a second optical means including said first optical means,
   a mirror and a lens system,
   a spectrograph for analysing the absorption spectrum of said simple material,
   said mirror being arranged in the path of the beam of coherent light between said laser light source and said optical focusing means, and being inclined relative to the light propagation direction of said coherent light,
   said mirror being transparent to the laser light employed, and being reflective to said radiation emitted from said focal spot and passing said optical focusing means,
   said lens being for focusing said radiation emitted from said focal spot into the aperture of said spectrograph.

2. An arrangement as claimed in claim 1, wherein an optical system is provided which focuses the light emitted from the target material cloud into an additional spectrograph aperture for analysing the emission spectrum of the target material at right angles to the propagation direction of the focused coherent laser light beam.

3. An arrangement as claimed in claim 1, wherein the optical focusing means is a lens objective.

4. An arrangement as claimed to claim 1, wherein said optical focusing means is a mirror system having a central obscuration.

* * * * *